US011253440B2

(12) United States Patent
Ketyer et al.

(10) Patent No.: US 11,253,440 B2
(45) Date of Patent: Feb. 22, 2022

(54) MOLDABLE GEL CLEANSER

(71) Applicant: Johnson & Johnson Consumer Inc., Skillman, NJ (US)

(72) Inventors: Cameron Ketyer, State College, PA (US); Joseph James Greco, South Plainfield, NJ (US); Bashar Oussama Salah, Plainsboro, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/787,984

(22) Filed: Feb. 11, 2020

(65) Prior Publication Data
US 2020/0261328 A1 Aug. 20, 2020

Related U.S. Application Data

(60) Provisional application No. 62/806,024, filed on Feb. 15, 2019.

(51) Int. Cl.
| | |
|---|---|
| *C11D 1/00* | (2006.01) |
| *C11D 3/38* | (2006.01) |
| *A61K 8/19* | (2006.01) |
| *A61K 8/65* | (2006.01) |
| *A61K 8/73* | (2006.01) |
| *A61K 8/04* | (2006.01) |
| *A61K 8/34* | (2006.01) |
| *A61K 8/41* | (2006.01) |
| *A61K 8/46* | (2006.01) |
| *A61K 8/60* | (2006.01) |
| *A61Q 19/10* | (2006.01) |

(52) U.S. Cl.
CPC ........... *A61K 8/042* (2013.01); *A61K 8/046* (2013.01); *A61K 8/19* (2013.01); *A61K 8/345* (2013.01); *A61K 8/416* (2013.01); *A61K 8/463* (2013.01); *A61K 8/602* (2013.01); *A61K 8/73* (2013.01); *A61Q 19/10* (2013.01)

(58) Field of Classification Search
CPC ......... C11D 1/00; C11D 3/2041; C11D 3/228; C11D 3/38; A61K 8/042; A61K 8/19; A61K 8/345; A61K 8/602; A61K 8/65; A61K 8/73; A61K 8/733; A61K 2800/48
See application file for complete search history.

(56) References Cited

U.S. PATENT DOCUMENTS

| | | | |
|---|---|---|---|
| 9,028,872 B2 | 5/2015 | Gaserod et al. | |
| 10,064,881 B2 | 9/2018 | Silberstein et al. | |
| 2001/0056049 A1* | 12/2001 | Aronson | C11D 3/2065 510/130 |
| 2004/0151683 A1* | 8/2004 | Kalbfleisch | A61K 8/73 424/70.13 |
| 2008/0206273 A1 | 8/2008 | Ambrosen et al. | |

FOREIGN PATENT DOCUMENTS

| | | | | |
|---|---|---|---|---|
| EP | 0271131 B1 | 6/1988 | | |
| FR | 2954162 A1 | 6/2011 | | |
| WO | WO 2006/067400 | | 12/2001 | |
| WO | WO 2006/067400 | * | 6/2006 | ............... A61K 8/73 |

OTHER PUBLICATIONS

The Croda Group of Companies, "Research Disclosure-Transformative Textures", vol. 656, No. 82, Dec. 2018, pp. 1353.
Mintel Report Record ID No. 6184579; Radiance Refreshing Jelly Mask; Date Published: Dec. 2018.
Mintel Report Record ID No. 5614603; Sulphate-Free Shower Shampoo; Date Published: Apr. 2018.
Thrimawithana, T.R. et al., "Texture and Rheological Characterization of Kappa and Iota Carrageenan in the presence to f Counter Ions", Carbohydrate Polymer vol. 82, (2010) pp. 69-77. (https://doi.org/10.1016/j.carbpol.2010.04.024).
Cargill Beauty, "Unleashing Nature Sustainably", Mar. 2017. (http://www.chembuyersguide.com/images/ cargill.pdf).
CPKelco GENU® Carrageenan Book (2002). (http://www.bisi.cz/cmsres.axd/get/cms$7CVwRhc3USVqgzxkKF96gl$2BChNrXcTg$BOUdiEtz5TfYA$2Fq1ADRHMfXfdEjUsYQaggUs9N6byPOkok$3D).
Shimadzu Testing Machine/Market News No. 011; Evaluation of Jelly Strength (Bloom Value), Jan. 2014. (https://www.shimadzu.com/an/industry/foodbeverages/n9j25k00000dqazu.htm).
Hernandez, M., et al., "Viscous Synergism in Carrageenans (k and y) and Locust Bean Gum Mixtures: Influence of Adding Sodium Carboxymethylcellulose, Published Oct. 2, 2001. vol. 7 issue: 5, pp. 383-391." Kappa carrageenan, Potassium salt form: Gels, face masks, shower gels, emulsions: Forms firm and brittle gels, CP Kelco Best Choice Guidelines (2012) (https://journals.sagepub.com/doi/abs/10.1106/6BCX-6XH6-PT82-8WCK.
https://www.cpkelco.com/wp-content/uploads/2012/08/FoodCatalog.pdf).
CPKelco, A Huber Company, "Sensorial Pleasures from Nature-Based Ingredients". (https://www.in-cosmetics.com/RXUK/RXUK_InCosmetics/2014-website/Documents/CP%20Kelco%20presentation_final.pdf?v=635340307802890491).
PCT International Search Report for PCT/IB2020/051095 dated May 15, 2020.

* cited by examiner

*Primary Examiner* — Brian P Mruk
(74) *Attorney, Agent, or Firm* — Laura A. Donnelly

(57) ABSTRACT

A moldable gel cleanser comprising a carrageenan, a source of potassium and a glycol is disclosed.

8 Claims, No Drawings

MOLDABLE GEL CLEANSER

This application claims benefit to provisional application Ser. No. 62/806,024, filed on Feb. 15, 2019, the entire contents of which are incorporated by reference herein.

FIELD OF THE INVENTION

The present invention relates to a personal care product particularly a moldable gel cleanser that has improved properties.

BACKGROUND OF THE INVENTION

Consumers like foam producing products for a variety of personal care uses, such as hair and body shampoos, facial cleansers and shave preparation gels. Foam based personal care products have a pleasant feel. Consumers particularly like high and thick foams, quick foaming action, lasting foams, and the feel of rich, luxurious, creamy foams. To achieve these desirable effects, surfactants are added to many personal care products. Surfactants play a major role in foam producing products by lowering the dynamic surface tension of the liquid-air interface to allow gas bubbles to be formed or introduced beneath the surface of the liquid. Surfactants also stabilize the foam once it is formed. However, surfactants are not without disadvantages. For example, some surfactants, such as sulfates, including alkyl sulfates and alkyl ether sulfates, are known to be irritating to the skin.

It is known that you can produce cosmetic jellies by mixing a surfactant with an extract of seaweed. Such products have been sold commercially but have not been widely adopted, at least in part due to the properties of the jelly. That is, the known cosmetic jellies have a semi-liquid form and when, for example, applied to the human body with water they break down into the consistency of a lumpy paste.

U.S. Published Application No. 20080206273 to Cosmetic Warriors, Ltd. discloses a cosmetic product that contains surfactant, glycerine, monopropylene glycol and optionally carrageenan. The reference discloses that the inclusion of monopropylene glycol, mixed with the glycerine, has an effect upon the consistency of the jelly, resulting in the jelly having a durable and almost rubber-like texture. The reference also discloses that the effects are surprising when the jelly contains a seaweed extract, since it was thought that such an extract would be destabilised by the presence of glycerine and monopropylene glycol. This U.S. application, which corresponds to International Published Application No. WO2006067400, was abandoned in 2010.

U.S. Pat. No. 9,028,872 to FMC Corporation discloses a foam, methods of preparation, and uses thereof. The reference discloses that the foam, which may be used in personal care applications, is preferably a polysaccharide and that examples of suitable polysaccharides for producing the foam include alginates, pectins, carrageenans, hyaluronates, chitosan and mixtures thereof.

U.S. Pat. No. 10,064,881 to Y&B Mother's Choice Ltd. discloses compositions containing naturally-obtained plant extracts that contain naturally-obtained saponin material. The reference discloses that carrageenan may be employed as a thickening agent in the compositions.

The present invention seeks to improve upon the previously known cosmetic jellies.

SUMMARY OF THE INVENTION

Toddlers struggle to form healthy hand washing habits. If caregivers use a fun, effective cleanser on children from birth, the children will recall positive experiences with it, and will be inclined to wash their hands with it going forward. The moldable gel cleanser of the invention, which is in fun, sensory-rich formats, promotes healthy handwashing habits.

This invention is a gel cleanser of a moldable format and texture having an amount of carrageenan effective to create an enriched sensory experience for the consumer. Further, the moldable gel cleanser is free of sulfates, so it is mild for babies and toddlers. The moldable gel cleanser has a gel matrix due to the presence of a potassium ion, and as such, the moldable gel cleanser has a gelatinous texture. The moldable gel cleanser contains glycol, which prevents sponginess, helps with the stability and structure of, and imparts a smooth surface to, the moldable gel cleanser.

According to a first aspect of the present invention there is provided a personal care product comprising:

a carrageenan, a source of potassium ions; and a glycol.

Carrageenan acts as a gelling agent. The form of the moldable gel cleanser may differ depending on the amount of carrageenan in the product. The carrageenan can be a blend of carrageenan containing kappa carrageenan and iota carrageenan. Depending on the ratio of kappa carrageenan and iota carrageenan, different forms, textures, fix syneresis and freeze thaw stability are achieved.

Strong, Durable Multi-Use Form

To form a strong, durable multi-use jelly cleanser, preferably, the personal care product contains at least 1.5%, but less than 2.0% kappa carrageenan. Not having enough carrageenan will cause the moldable gel cleanser to crumble upon use, while having too much carrageenan will compress the gel matrix and make it less gelatinous, minimizing the sensory experience. Most preferably, the personal care product having this form contains 1.75% kappa carrageenan.

Crushable, Single Use (Crumble) Form

To form a crushable, single-use jelly cleanser having a crumble texture, preferably, the personal care product contains about 0.63% to about 0.75% kappa carrageenan. $CaCl_2$) at 0.1%-0.5%, which makes kappa carrageenan brittle and crumbly, can be used to increase surface area post crush in the crumble form.

Jell-O®-Like Form

To form a Jell-O®-like jelly cleanser, preferably, the personal care product contains 1.5% to 2.0%, and more preferably 1.75%, carrageenan in a ratio of 50:50-75:25 iota carrageenan:kappa carrageenan. Iota carrageenan:kappa carrageenan in ratio of 75:25 results in a smooth jello texture. More preferably, the blend of carrageenan contains kappa carrageenan:iota carrageenan in a ratio of 0.88:2.62.

Preferably, the personal care product contains 0.25% to 1.0%, and more preferably 0.5%, of a source of potassium ion. Preferably, the source of potassium ion is potassium sorbate. The potassium sorbate also acts as preservative in the moldable gel cleanser of the invention.

Preferably, the personal care product contains 2.5% to 7%, more preferably 5% to 6%, glycol. Preferably, the glycol is butylene glycol. Glycol acts as a humectant in the moldable gel cleanser of the invention.

Preferably the personal care product also contains 10% to 30%, more preferably 15% to 25%, surfactant. Thus, according to another aspect of the present invention there is provided a personal care product comprising:
- a carrageenan,
- a source of potassium ions;
- a glycol; and
- a surfactant.

Preferably, the surfactant is a surfactant system that comprises sodium methyl cocoyl taurate, cocamidopropyl betaine and decyl glucoside. More preferably, the surfactant system comprises sodium methyl cocoyl taurate, cocamidopropyl betaine and decyl glucoside in a 1:2:1 (anionic:amphoteric:non-ionic) ratio. Decyl glucoside boosts foaming in the moldable gel cleanser of the invention.

According to another aspect of the present invention there is provided a method of manufacturing a personal care product comprising: a carrageenan, a source of potassium ion, a glycol, and, preferably, a surfactant.

According to another aspect of the present invention the surface area of the moldable gel cleanser can be maximized to enhance foaming and decrease slip.

The inventors hereof have discovered that the inclusion of carrageenan, potassium ions and glycol has a remarkable effect upon the consistency of the moldable gel cleanser.

The strong, durable multi-use form of the moldable gel cleanser of the present invention is particularly useful as a personal care product because it does not readily breakdown in the way that a conventional cosmetic jelly does. It is therefore particularly suitable for use as a shower gel or body wash, where it can be applied in a somewhat similar fashion to a conventional bar of soap. All of the moldable gel cleanser forms are also suitable for use as, for example, a hair wash.

DETAILED DESCRIPTION OF THE INVENTION

Definitions

"Carrageenans" are linear sulfated polysaccharides that are extracted from red edible seaweeds. Carrageenans are chains of D-galactopyranosyl units joined with alternating α-1,3 and β-1,4 glycosidic linkages. There are three main varieties of carrageenan, which differ in their degree of sulfation. Kappa-carrageenan has one sulfate group per disaccharide, iota-carrageenan has two, and lambda-carrageenan has three.

"Flash foaming" refers to the foam formation behavior of a substance during foaming, i.e., the amount of foam produced dependent on time or energy input.

"Gel" is a soft, partially transparent semisolid substance.

"Gelling agent" is a substance added to a composition to provide the texture of a gel.

"Humectant" is a substance that retains moisture.

"Sulfate" is a salt that forms when sulfuric acid reacts with another chemical. It's a broader term for other synthetic sulfate-based chemicals that consumers may be concerned about, such as sodium lauryl sulfate (SLS) and sodium laureth sulfate (SLES). These compounds, which are produced from petroleum and plant sources such as coconut and palm oil, are found in cleaning and personal care products. The main use for SLS and SLES in products is to create lather.

"Surfactants" are compounds that lower the surface tension (or interfacial tension) between two liquids, between a gas and a liquid, or between a liquid and a solid. Surfactants may act as detergents, wetting agents, emulsifiers, foaming agents, and dispersants.

"Syneresis" is the contraction of a gel accompanied by the separation out of liquid.

It was observed that a combination of carrageenan and a source of potassium ions formed strong, clear, gels and was capable of supporting a surfactant system.

It was also observed that specific ratios of carrageenan types impact texture, syneresis, freeze/thaw stability, and crumbling.

It was also observed that a specific combination of surfactants enhances the cleansing aspects of the product (e.g., flash foaming, foam longevity, foam quality/density, mildness and skin afterfeel).

The present invention achieves a balance between appropriate foam profile, while remaining gentle and mild enough to leave skin soft and conditioned.

Embodiments of the present invention will now be described by way of further example only.

A moldable gel cleanser according to an embodiment of the present invention is formed from components in Table 1, wherein percentages are given by weight.

TABLE 1[1]

| INCI Name | Formula | | | | | | | |
|---|---|---|---|---|---|---|---|---|
| | 008 | 009 | 012 | 020 | 022 | 026 | 029 | 030 |
| Water | 61.9 | 63.65 | 56.4 | 60.35 | 66.725 | 65.48 | 61.3 | 62.3993 |
| Sodium Benzoate | 0.5 | 0.5 | 0.5 | 0.5 | 0.5 | N/A | 0.5 | 0.5 |
| Potassium sorbate | 0.5 | 0.5 | 0.5 | 0.5 | 0.5 | 0.5 | 0.5 | 0.5 |
| Glycerin | 6 | 5 | 5 | 6 | 6 | 6 | 6 | 6 |
| Carrageenan extract (Genugel CG-130[2]) | 1.75 | 1.75 | 1.75 | 1.75 0.8 Iota[3] | 1.75 | 1.75 | 1.75 | 1.75 |
| Sodium Methyl Cocyl Taurate | 9.7 | 7.3 | 15 | 15 | 7.3 | 5.42 | 7.3 | 7.3 |
| Cocamidopropyl betaine | 13.3 | 15 | N/A[7] | N/A[8] | 10 | 11.6 | 10 | 10 |
| Decyl glucoside | N/A | N/A | N/A | 3.25 | N/A | 3.25 | N/A[9] | 3.5 |
| Ethylhexyl-glycerin; Phenoxyethanol | 0.6 | 0.6 | 0.6 | 0.6 | 0.6 | 0.6 | 0.6 | 0.6 |
| Butylene Glycol | 5 | 5 | 5 | 6 | 6 | 5 | 5 | 6 |
| Fragrance | 0.5 | 0.3 | 1 | 0.5 | 0.5 | 0.3 | 0.5 | 0.5 |
| Dye | N/A | 2 | 2 | N/A | N/A | N/A | N/A | 0.0007 |
| 50% citric acid solution | 0.25 | 0.1 | 0.25 | N/A | 0.125 | 0.1 | 0.25 | 0.95 |
| Total: | 100 | 100 | 100 | 100 | 100 | 100 | 100 | 100 |

TABLE 1[1]-continued

| INCI Name | Formula | | | | | |
|---|---|---|---|---|---|---|
| | 031 | 061 | 117 | 119 | 120 | 172 |
| Water | 68.4 | 68.05 | 60.26 | 60.26 | 62.26 | 58.25965 |
| Sodium Benzoate | 0.5 | 0.5 | N/A | N/A | N/A | N/A |
| Potassium sorbate | 0.5 | 0.5 | 0.5 | 0.5 | 0.5 | 0.5 |
| Glycerin | 6 | 6 | 6 | 6 | 8 | 8 |
| Carrageenan extract (Genugel CG-130[2]) | 1.75 | 1.75 | 1.75 | 1.225 [4] | 1.75 | 1.75 |
| Sodium Methyl Cocyl Taurate | N/A[5] | N/A[6] | 8.85 | 8.85 | 8.85 | 8.85 |
| Cocamidopropyl betaine | 10 | N/A | 12.14 | 12.14 | 12.14 | 12.14 |
| Decyl glucoside | 3.5 | 9.3 | 4.5 | 4.5 | 4.5 | 4.5 |
| Ethylhexyl-glycerin; Phenoxyethanol | 0.6 | 0.6 | 0.6 | 0.6 | 0.6 | 0.6 |
| Butylene Glycol | 6 | 5 | 5 | 5 | N/A[10] | 5 |
| Fragrance | 0.5 | 0.5 | 0.3 | 0.3 | 0.1 | 0.3 |
| Dye | N/A | N/A | N/A | N/A | N/A | 0.00035 |
| 50% citric acid solution | 0.25 | N/A | 0.1 | 0.1 | 0.1 | 0.1 |
| Total: | 100 | 100 | 100 | 100 | 100 | 100 |

[1] All ingredients are in (wt %).
[2] See attached CP Kelco Product Data Sheet Genugel carrageenan CG-130 (2011).
[3] Genuviso CG-131.
[4] Genu Gum type RL-60Z 0.525.
[5] Sodium Hydrolyzed Potato Starch Dodecenylsuccinate 2%.
[6] Potassium Cocoyl Glycinate 7.8%.
[7] Sodium Lauryl Sarcosinate 12%.
[8] Water; Cocamidopropyl Hydroxysultaine; Sodium Chloride 8%.
[9] Sodium Lauroyl Sarcosinate 5.3%
[10] Glucam E-10 Humectant 1%.

Each of the formulas were tested for a number of criteria to determine acceptability. Results are in Table 2 below.

TABLE 2

| Formula # | Surfactant Combination and Ratios | Trade Names | % Kappa Carrageenan | Trade Name | Other Polymer % and Trade Name | Formed Gel Matrix Capable of pouring and Being Molded (pass/fail) | Met Aesthetic Release Criteria (pass/fail) | Met minimum foam height threshold (pass/fail) (380 mL) |
|---|---|---|---|---|---|---|---|---|
| 008 | 1:2 SMCT:CAPB | Adinol CT24-LQ-(RB), TEGO Betain F 50 | 1.75 | Genugel CG-130 | N/A | Pass | Pass | N/A |
| 009 | 1:3 SMCT:CAPB | Adinol CT24-LQ-(RB), TEGO Betain F 50 | 1.75 | Genugel CG-130 | N/A | Pass | Pass | N/A |
| 012 | 1:1 SMCT:Sarcosinate | Adinol CT24-LQ-(RB), Crodasinic LS30 | 1.75 | Genugel CG-130 | N/A | Pass | Pass | N/A |
| 020 | 1:1 SMCT:CAPHS | Adinol CT24-LQ-(RB), Mirataine CBS | 1.75 | Genugel CG-130 | I-Carrageenan, 0.8, Genuvisco CG-131 | Pass | Pass | Pass |
| 022 | 2:1 SMCT:CAPHS | Adinol CT24-LQ-(RB), Mirataine CBS | 1.75 | Genugel CG-130 | N/A | Pass | Pass | N/A |
| 026 | 1:3:1 SMCT:CAPB:DG | Adinol CT24-LQ-(RB), TEGO Betain F 50, Plantaren 2000 | 1.75 | Genugel CG-130 | N/A | Pass | Pass | Pass |

TABLE 2-continued

| Formula # | Surfactant Combination and Ratios | Trade Names | % Kappa Carrageenan | Trade Name | Other Polymer % and Trade Name | Formed Gel Matrix Capable of pouring and Being Molded (pass/fail) | Met Aesthetic Release Criteria (pass/fail) | Met minimum foam height threshold (pass/fail) (380 mL) |
|---|---|---|---|---|---|---|---|---|
| 029 | 1:1:2 SMCT:Sarcosinate:CABP | Adinol CT24-LQ-(RB), Crodasinic LS30, Plantaren 2000 | 1.75 | Genugel CG-130 | N/A | Pass | Pass | Pass |
| 030 | 1:2:1 SMCT:CAPB:DG | Adinol CT24-LQ-(RB), TEGO Betain F 50, Plantaren 2000 | 1.75 | Genugel CG-130 | N/A | Pass | Pass | Pass |
| 031 | 1:2:1 PS-111:CAPB:DG | Structure PS-111, TEGO Betain F 50, Plantaren 2000 | 1.75 | Genugel CG-130 | N/A | Pass | Pass | N/A |
| 061 | 1:2 PC Glycinate | Amilite GCK 12H | 1.75 | Genugel CG-130 | N/A | Fail | Fail | N/A |
| 117 | 1:2:1 SMCT:CAPB:DG | Adinol CT24-LQ-(RB), TEGO Betain F 50, Plantaren 2000 | 1.75 | Genugel CG-130 | N/A | Pass | Pass | Pass |
| 119 | 1:2:1 SMCT:CAPB:DG | Adinol CT24-LQ-(RB), TEGO Betain F 50, Plantaren 2000 | 1.225 | Genugel CG-130 | Locust Bean Gum (Genu Gum RL 200Z CG) 0.525% | Pass | Fail | N/A |
| 120 | 1:2:1 SMCT:CAPB:DG | Adinol CT24-LQ-(RB), TEGO Betain F 50, Plantaren 2000 | 1.75 | Genugel CG-130 | N/A | Pass | Fail | N/A |

A crushable, single use (crumble) moldable gel cleanser according to an embodiment of the present invention is formed from components in Table 3, wherein percentages are given by weight.

TABLE 3

Crumble 1:2:1 SMCT:CAPB:DG crumble 8% glycerin

| US INCI Name | Percentage |
|---|---|
| Water | 59.32965 |
| Potassium Sorbate | 0.5 |
| Glycerin | 8 |
| Genugel CG-130 | 0.68 |
| Sodium Methyl Cocoyl Taurate; Water | 8.85 |
| Cocamidopropyl Betaine | 12.14 |
| Decyl Glucoside | 4.5 |
| Ethylhexylglycerin; Phenoxyethanol | 0.6 |
| Butylene Glycol | 5 |
| Fragrance | 0.3 |
| Red 40 | 0.00035 |
| Citric Acid | 0.1 |

A Jell-O®-like moldable gel cleanser according to an embodiment of the present invention is formed from the components in Table 4, wherein percentages are given by weight.

TABLE 4

| US INCI Name | Percentage |
|---|---|
| Water | 61.85 |
| Sodium Benzoate | 0.5 |
| Potassium Sorbate | 0.5 |
| Glycerin | 6 |
| Genugel Carrageenan CG-130 | 0.88 |
| Satiagel VPC 508 (Cargill, iota carrageenan) | 2.62 |
| Sodium Methyl Cocoyl Taurate; Water | 7.3 |
| Cocamidopropyl Betaine | 10 |
| Decyl Glucoside | 3.5 |
| Ethylhexylglycerin; Phenoxyethanol | 0.6 |
| Butylene Glycol | 5 |
| Fragrance | 0.5 |
| Calcium Chloride | 0.75 |

A method of manufacturing a moldable gel cleanser according to the present invention and based upon the above stated groups of components is as follows:

1. Add 100% purified water at ambient temperature and begin mixing.
2. Add sodium benzoate (if in formula) and mix until fully dissolved.
3. Add potassium sorbate and mix until fully dissolved.
4. Add glycerin and mix until uniform.
5. Begin heating to 80-85° C.
6. Add Genugel GC-130 and mix until uniform.

7. Add sodium methyl cocoyl taurate (or substitute) at 80° C. and mix until uniform.
8. Add cocamidopropyl betaine (if in formula or substitute) and mix until uniform.
9. Add decyl glucoside (if in formula) and mix until uniform.
10. Begin cooling to 65° C.
11. Add ethylhexyl-glycerin; phenoxyethanol and mix until uniform.
12. Add dye solution dropwise to desired shade.
13. Use citric acid to adjust pH to 5.5-5.7.
14. Pour solution in to molds if desired.

The above stated method is an example only and may be varied depending on the specific components used.

The present inventors determined that:

Carrageenan forms solid jellies.

Potassium sorbate is a good preservative/crosslinker.

1.5%-2% kappa carrageen works well in the strong, durable multi-use and the Jell-O® forms.

1.75% kappa carrageenan works best in the strong, durable multi-use and the Jell-O® forms.

Glycinates are incompatible, as demonstrated using potassium cocoyl glycinate.

Iota carrageenan does not work well on its own. A blend of iota carrageenan and kappa carrageenan works well.

PEG-80 and any polyethoxylated chemicals are incompatible with carrageenan.

The optimal carrageenan ratio for an iota/kappa blend is 0.88:2.62.

Example

Surfactants were tested. The results are shown in Table 5. As can be seen below, not all surfactants are compatible with the moldable gel cleanser of the invention.

TABLE 5

| Surfactant | Results |
| --- | --- |
| Sodium methyl cocoyl taurate (SMCT) | Optimal foaming and density |
| Sodium lauryl sarcosinate | Flash foam inferior to SMCT |
| K/Na cocoyl glycinate | Incompatible with carrageenan |
| PS-111 | Foam booster |
| Sodium cocoyl isethionate | Incompatible with carrageenan |
| Cocamidopropyl betaine | Best flash foaming/quality |
| Cocamidopropyl hydroxysultaine | Foam too dense/creamy |
| Disodium amphodiacetate | Amphoacetates incompatible with carrageenan |
| Sodium lauroamphoacetate | Amphoacetates incompatible with carrageenan |
| Decyl glucoside | Boosts foam, enhances mildness |
| PEG-80 sorbitan laurate | Polyethoxylation incompatible with carrageenan |
| Cocoglucoside | Inferior to decyl glucoside |

Example

Foam Height

Foam height testing is a valuable method to objectively quantify foaming performance. It is performed by a tumbling instrument to ensure reproducibility. This method involves inverting cylinders for 32 cycles with 90 g water and 10 g product. Data are collected after 2, 4, 8, 16 and 32 cycles.

More foam is preferred.
Flash foaming is important.
Cycles 2-8, 16-32.
Helpful to quantify cleanser performance.

Example

Syneresis Experiment Method
1. Create batch and pour (2) semi-sphere samples, allow to fully cool.
2. Once cool, record masses.
   a. If testing open-air, continue with steps 3-11.
   b. If testing enclosed, go to step 12.
3. Obtain one standard tongue depressor and record its mass.
4. Stick tongue depressor through one of the jelly, so that the stick is parallel with the flat side of the semi-sphere.
5. Record mass of jelly+stick.
6. Lay tongue depressor across mouth of 400 mL beaker, so jelly is suspended in air.
7. Record current time.
8. In 24 hours, record mass of sample+stick.
9. In 48 hours, record mass of sample+stick.
10. In 72 hours, record mass of sample+stick.
11. After 3 days, calculate % mass lost per day.
12. Obtain 8 oz jar and record mass.
13. Add jelly to jar flat side down.
14. In 24 hours, remove jelly WITHOUT inverting jar.
15. Dry completely and measure mass.
16. In 48 hours, remove jelly WITHOUT inverting jar
17. Dry completely and measure mass.
18. In 72 hours, remove jelly WITHOUT inverting jar.
19. Dry completely and measure mass.
20. After 3 days, calculate % mass lost per day.

Example

EIT Testing

EIT (epithelial irritation testing) can be used to assess if the systems are mild enough for use on infants and toddlers.

Example

The following observations can be made to assess the aesthetics of the moldable gel cleanser:

Foam quality
Foam density
Flash foam
Dry down
Rinse-off
Residue
Texture

It will be understood that, while various aspects of the present disclosure have been illustrated and described by way of example, the invention claimed herein is not limited thereto, but may be otherwise variously embodied according to the scope of the claims presented in this and/or any derivative patent application.

REFERENCES

CPKelco GENU® Carrageenan Book (2002), http://www.bisi.cz/cmsres.axd/get/cms$7CVVwRhc3USVqgzxkKF96gI$2BChNrXcTq$2BOUdiEtz5TfYA$2Fg1ADRHMfXfdEjUsYQagpUs9N6byPOkok$3D.

T. R. Thrimawithana et al., Texture and rheological characterization of kappa and iota carrageenan in the presence of counter ions, Carbohydrate Polymers, Volume 82, Issue 1, 2 Aug. 2010, Pages 69-77, https://doi.org/10.1016/j.carbpol.2010.04.024 and https://www.sciencedirect.com/science/article/pii/S0144861710002894.

Shimadzu Evaluation of Jelly Strength (Bloom Value), https://www.shimadzu.com/an/industry/foodbeverages/n9j25k00000dqazu.htm.

M. J. Hernánadez et al., Viscous Synergism in Carrageenans (κ and λ) and Locust Bean Gum Mixtures: Influence of Adding Sodium Carboxymethylcellulose, https://journals.sagepub.com/doi/abs/10.1106/6BCX-6XH6-PT82-8WCK.

"Kappa carrageenan, Potassium salt form: Gels, face masks, shower gels, emulsions: Forms firm and brittle gels, CP Kelco Best Choice Guidelines (2012), https://www.cpkelco.com/wp-content/uploads/2012/08/FoodCatalog.pdf.

See also CP Kelco Sensorial pleasures from nature-based ingredients, https://www.in-cosmetics.com/RXUK/RXUK_InCosmetics/2014-website/Documents/CP%20Kelco%20presentation_final.pdf?v=635340307802890491.

Cargill Beauty Unleashing Nature Sustainably, http://www.chembuyersguide.com/images/cargill.pdf.

The invention claimed is:

1. A solid jelly personal care product comprising:
a carrageenan;
a source of potassium ions;
a glycol; and
a surfactant system, wherein the surfactant system comprises sodium methyl cocoyl taurate, cocamidopropyl betaine and decyl glucoside.

2. The solid jelly personal care product of claim 1, wherein the carrageenan is kappa carrageenan.

3. The solid jelly personal care product of claim 1, wherein the percentage by weight of carrageenan is about 1.5% to less than 2.0%.

4. The solid jelly personal care product of claim 2, wherein the percentage by weight of kappa carrageenan is about 1.75%.

5. The solid jelly personal care product of claim 1, wherein the percentage by weight of a source of potassium ion is about 0.25% to about 1.0%.

6. The solid jelly personal care product of claim 1, wherein the percentage by weight of glycol is about 2.5% to about 7.0%.

7. The solid jelly personal care product of claim 1, wherein the personal care product is a moldable gel cleanser in a form selected from the group consisting of strong, durable multi-use jelly cleanser; crushable, single use jelly cleanser; and gelatinous jelly cleanser.

8. A method of forming a solid jelly personal care product comprising the steps of selecting the components of the product to include a carrageenan; a source of potassium ions; a glycol; and a surfactant system, wherein the surfactant system comprises sodium methyl cocoyl taurate, cocamidopropyl betaine and decyl glucoside.

* * * * *